(12) United States Patent
Leatt et al.

(10) Patent No.: US 7,846,117 B2
(45) Date of Patent: Dec. 7, 2010

(54) NECK BRACE

(75) Inventors: Christopher James Leatt, Cape Town (ZA); Grant Leigh Nelson, Cape Town (ZA); Mark Eric Hopkins, Cape Town (ZA)

(73) Assignee: Leatt Corp., Inc., Las Vegas, NV (US)

( * ) Notice: Subject to any disclaimer, the term of this patent is extended or adjusted under 35 U.S.C. 154(b) by 31 days.

(21) Appl. No.: 11/778,840

(22) Filed: Jul. 17, 2007

(65) Prior Publication Data
US 2008/0177209 A1 Jul. 24, 2008

Related U.S. Application Data

(63) Continuation-in-part of application No. 11/440,576, filed as application No. PCT/ZA2004/000148 on Nov. 26, 2004.

(30) Foreign Application Priority Data
Nov. 26, 2003 (ZA) .............................. 2003/9174

(51) Int. Cl.
*A61F 5/00* (2006.01)
(52) U.S. Cl. .................. 602/18; 128/DIG. 23
(58) Field of Classification Search ............. 602/17–19; 128/DIG. 23
See application file for complete search history.

(56) References Cited

U.S. PATENT DOCUMENTS 3,601,123 A * 8/1971 McFarland .................... 602/18
3,724,452 A * 4/1973 Nitschke ....................... 602/18
4,383,523 A * 5/1983 Schurman ..................... 602/36
5,371,905 A 12/1994 Keim
5,444,870 A 8/1995 Pinsen
7,141,031 B2 * 11/2006 Garth et al. .................... 602/18

FOREIGN PATENT DOCUMENTS

| WO | 03/015555 | 2/2003 |
| WO | 2005/051251 | 6/2005 |
| WO | 2007/120764 | 10/2007 |
| WO | 2008/050307 | 5/2008 |
| WO | 2008/105010 | 9/2008 |

OTHER PUBLICATIONS

PCT International Search Report for PCT/CH2008/052880 dated Dec. 18, 2008.

* cited by examiner

*Primary Examiner*—Michael A. Brown
(74) *Attorney, Agent, or Firm*—Connolly Bove Lodge & Hutz LLP

(57) ABSTRACT

Neck brace that inhibits excessive neck movement during impact, yet allows for a high degree of movement of the wearer's head during normal operation of the neck brace. May include impact surface(s) that limits movement of a helmet by contacting an underside of the helmet; bearing surface(s) configured for bearing on wearer; a structure between impact surface and bearing surface, sufficiently resilient to transfer impact loads of the helmet to the impact surface, to the wearer's body; wherein the impact surface is displaceable towards an adjacent part of the bearing surface and wherein the structure is configured to permit the displacement at rates slower than a predetermined rate of displacement and to resist the displacement if the rate of displacement exceeds the predetermined rate. May include a pivotal joint between the displaceable part and remainder of neck brace and impact brake element(s).

20 Claims, 4 Drawing Sheets

NECK BRACE

This application is continuation in part of U.S. Utility patent application Ser. No. 11/440,576 filed May 25, 2006 which is a national stage filing of international application PCT/ZA2004/000148 filed 26 Nov. 2004, published in English under PCT Article 21(2), which claims benefit from and is a Paris Convention filing of South African Patent Application Serial No. 2003/9174 filed 26 Nov. 2003, the specifications of which are all hereby incorporated herein by reference.

BACKGROUND OF THE INVENTION

1. Field of the Invention

This invention relates to protective equipment for inhibiting neck injuries while wearing a helmet. In particular, the invention relates to a neck brace.

2. Description of the Related Art

A device in the form of a neck brace is disclosed in International Patent Application No. PCT/ZA04/00148, which is intended to be worn around the neck and to receive impact loads from the bottom edge of a full face helmet and to transfer these loads to the wearer's body along a load path. The neck brace described in PCT/ZA04/00148 inhibits excessive movement of the helmet and thus of the wearer's head during impact, e.g. during a collision in motor sport.

The neck brace described in PCT/ZA04/00148 was designed to inhibit head and neck movement as little as possible during normal operation and it has achieved that purpose. However, in some exceptional cases, notably in high speed road motorcycling, the wearer needs to tilt the head more severely during normal operation, typically to achieve higher aerodynamics.

BRIEF SUMMARY OF THE INVENTION

One or more embodiments of the invention inhibit excessive neck movement during impact, yet allow for a high degree of movement of the wearer's head during normal operation of the neck brace.

According to the present invention there is provided a neck brace that includes:
  at least one impact surface which, when the brace is used with a helmet, limits movement of the helmet by contacting an underside of the helmet;
  at least one bearing surface which is shaped and configured for bearing on the body of a wearer of the brace;
  a structure that extends between the impact surface and the bearing surface, the structure being sufficiently resilient to transfer impact loads of the helmet on the impact surface, to the wearer's body; and,
  wherein at least part of the impact surface is displaceable towards an adjacent part of the bearing surface and wherein the structure is configured to permit the displacement at rates slower than a predetermined rate of displacement and to resist the displacement if the rate of displacement exceeds the predetermined rate.

The brace may include a pivotal joint between the displaceable part and the remainder of the neck brace and the pivotal joint may be configured to permit pivotal, as well as sliding displacement of the displaceable part relative to the remainder of the neck brace.

The neck brace may include a rear displaceable part at the rear of the neck brace which is downwardly pivotable towards the upper back of a wearer of the neck brace and may include a front displaceable part at the front of the neck brace which is downwardly pivotable towards the chest of the wearer and which may be configured to slide rearwards towards the wearer's chest during the pivotal movement.

The support structure may include at least one impact brake element extending between the displaceable part of the impact surface and the remainder of the structure.

The impact brake element may include:
  a first component which defines a first brake surface;
  a second component which defines a second brake surface and which is displaceable relative to the first component when the displaceable part is displaced relative to the neck brace, the first and second braking surfaces extending at an acute angle relative to each other;
  at least one lock element disposed between the first and second brake surfaces; and,
  the lock element being configured to allow movement between the first and second components at rates lower than a predetermined rate and to engage the first and second brake surfaces in a taper lock, when displacement between the two components occurs at a rate exceeding the predetermined rate.

The first brake surface may be a cylindrical surface and the second brake surface may be a frusto-conical surface. The first component may be an outer cylindrical sleeve and the second component may be elongate in shape and may be longitudinally displaceable with at least part of the second component inside the sleeve, the second component including a protuberance that protrudes outside the sleeve, at least at times. An annular recess may be defined around the second component of at least one the lock element and the second brake surface may be defined on the inner circumference the annular recess and at least one, but preferably a plurality of lock elements are held captive inside the annular recess.

BRIEF DESCRIPTION OF THE DRAWINGS

For a better understanding of the present invention, and to show how the same may be carried into effect, the invention will now be described by way of non-limiting example, with reference to the accompanying drawings in which.

DETAILED DESCRIPTION

Figure 1:
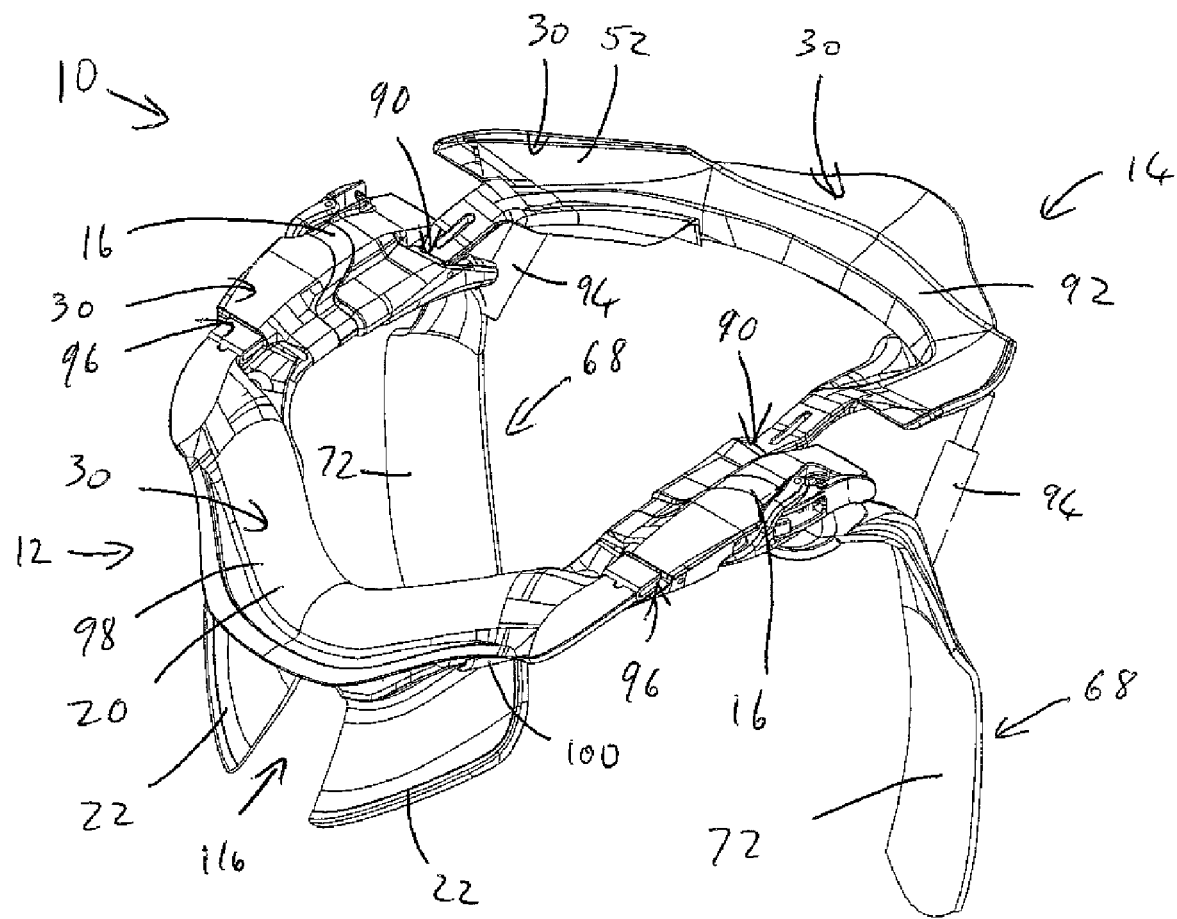
FIG. 1 is a three dimensional view from the front and from above, of a neck brace in accordance with the present invention.
Figure 2:
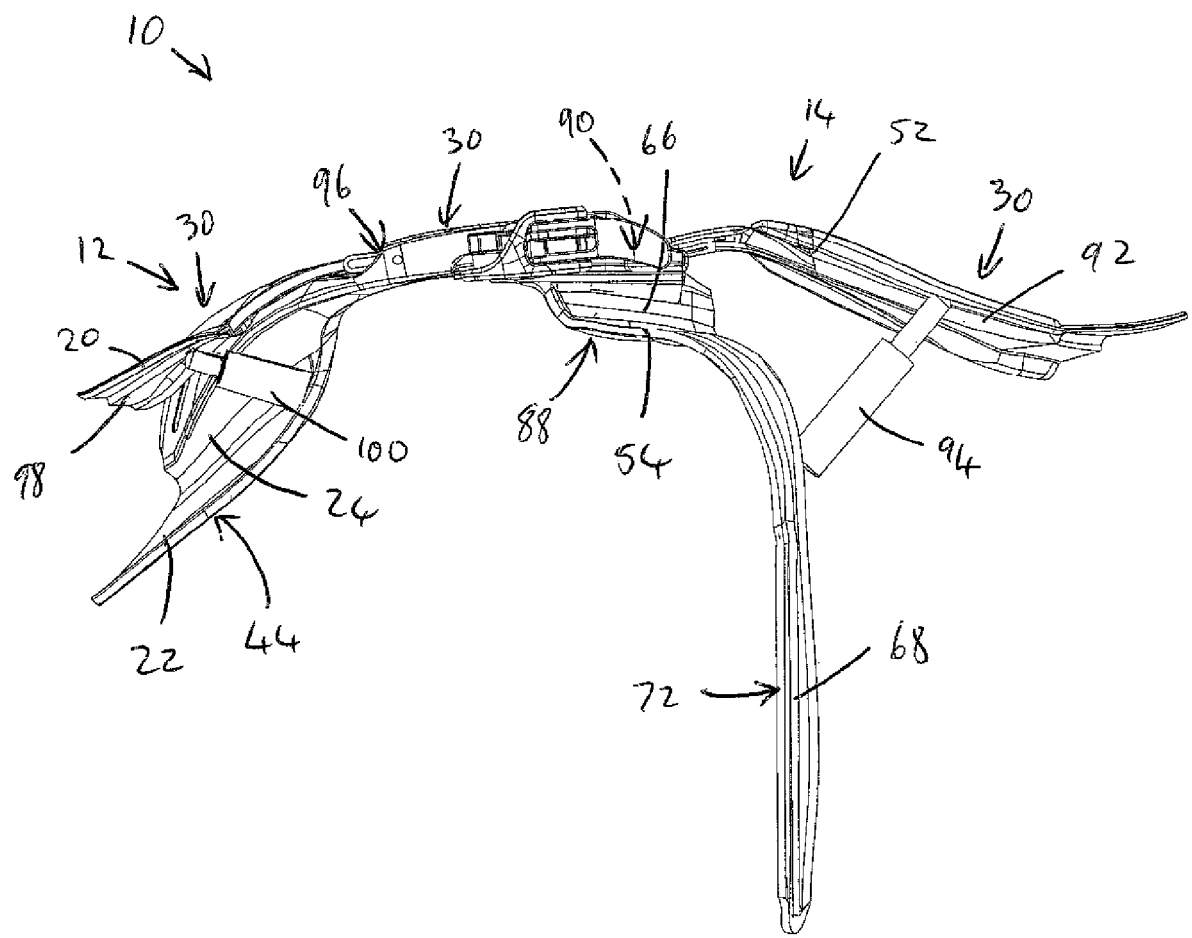
FIG. 2 is a side view of the neck brace of FIG. 1.
Figure 3:
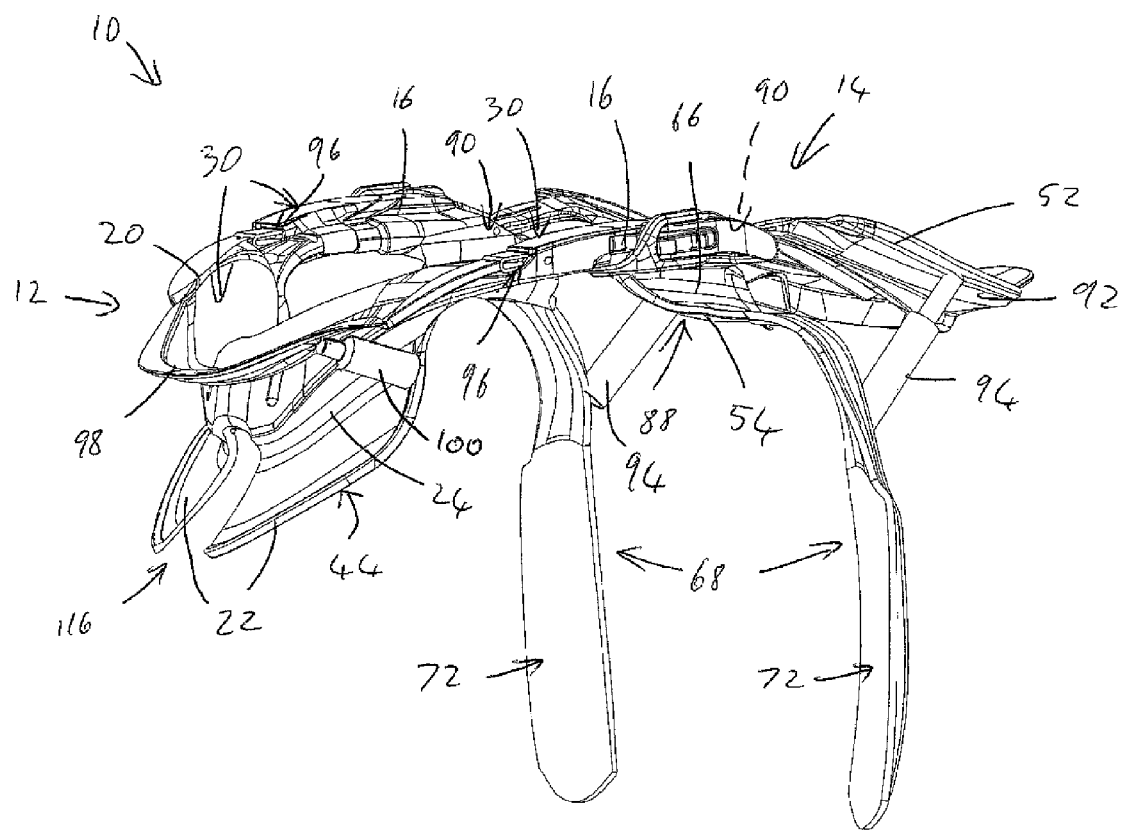
FIG. 3 is a three dimensional view of the neck brace of FIG. 1, taken from the front at an oblique angle.

Referring to FIGS. 1 to 3, a neck brace in accordance with the present invention is generally indicated by reference numeral 10.

The neck brace 10 includes a front section 12 and a rear section 14 which can be secured together at lateral hinge connectors 16 to form a ring that can extend around the neck of a wearer. The front section 12 is U-shaped in plan view and includes a top flange 20 defining part of a generally upwardly facing impact surface 30 that can receive impact loads from the bottom of a full face helmet worn by the wearer, a bottom flange 22 defining a cushioned chest bearing surface 44 that is configured to bear on the wearer's chest, and a structure in the form of a wall 24 that extends between the top and bottom flanges to transfer the impact loads from the helmet to the wearer's body.

The rear section 14 is also U-shaped in plan view and includes a top flange 52 that is generally a continuation of the top flange 20 of the front section, with an upwardly facing impact surface 30, and bottom flange 54 that is generally a continuation of the bottom flange 22 and that defines padded shoulder bearing surfaces 88 where it is configured to bear on the shoulders of the wearer. A structure in the form of a wall 66 extends between the top flange 52 and the bottom flange 54. The rear section further includes two bars 68 that each extends from the rear of the bottom flange 54 along the upper back of the wearer with a padded back bearing surface 72 for bearing on the back of the wearer.

The purpose of the top flanges 20 and 52 is to limit movement of the wearer's helmet during impact, e.g. during high speed motor sport accidents, by contacting the underside of the helmet with the impact surface 30 and transferring the impact load to the wearer's body via the chest, shoulder and back bearing surfaces 44,88,72 to reduce the risk of injury to the neck and upper spine of the wearer.

Embodiments of the invention may utilize two bars 68 as shown or any other number of bars as one skilled in the art will recognize as any number of bars 68 including one or more displaced at any point along bottom flange 54 may be utilized in keeping with the spirit of the invention.

Referring further to FIGS. 1 to 3, in the present invention, a rear part of the top flange 52 is pivotally connected to the remainder of the rear section 14 at pivotal joints 90, so that it forms a rear displaceable part 92 that can pivot downwards towards the upper back of the wearer, i.e. towards the shoulder and/or back bearing surfaces 88,72. Two impact brake elements 94 extend between the displaceable part 92 and each of the bars 68 to permit some pivotal movement in the joints 90, but to inhibit undesirable pivotal movement, as described in more detail below.

Similarly, a front part of the top flange 20 is pivotally connected to the remainder of the front section 12 at pivotal joints 96, so that it forms a front displaceable part 98 that can pivot downwards towards the chest of the wearer, i.e. towards the chest bearing surface 44. In addition, the pivotal joints 96 are configured to allow the rear ends of the displaceable part 98 to slide rearwards relative to the remainder of the front section 12 to allow the displaceable part to slide rearwards and/or pivot downwards. Two impact brake elements 100 extend between the displaceable part 98 and lateral locations on the bottom flange 22 to permit some pivotal and/or sliding movement in the joints 96, but to inhibit undesirable pivotal and/or sliding movement, as described in more detail below.

Figure 4A:
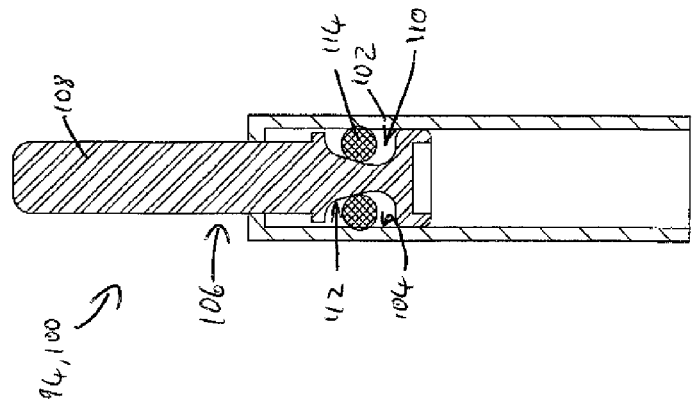
FIGS. 4A to 4C are sectional views through an impact brake element of the neck brace of FIG. 1, in three different operational conditions.
Figure 4B:
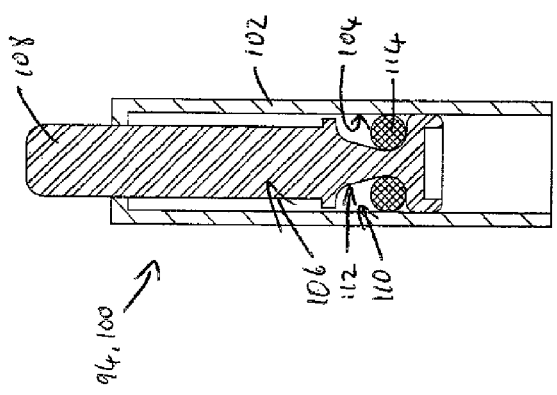
Figure 4C:
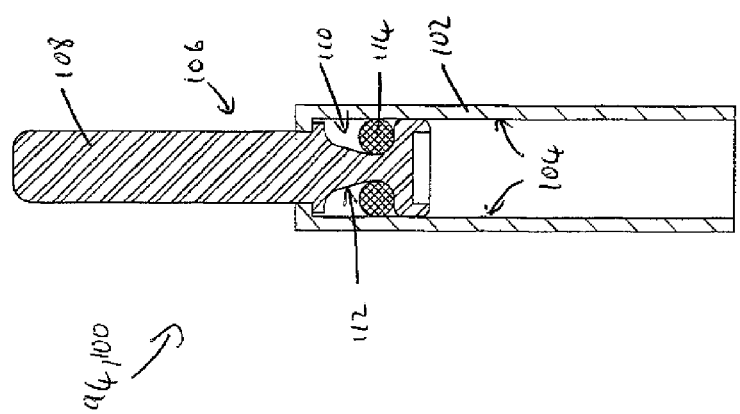

Referring to FIGS. 4A to 4C, each of the impact brake elements 94,100 includes a first component in the form of an outer cylindrical sleeve 102 which defines a first, cylindrical brake surface 104 on the inside of the sleeve and a second component in the form of an elongate probe 106, most of which is receivable inside the sleeve and which is longitudinally (i.e. axially) displaceable relative to the sleeve. The probe 106 has an elongate protuberance 108 at its upper end that protrudes outside the sleeve 102 by a degree that varies depending on the position of the probe inside the sleeve. The probe 106 defines an annular recess 110 on its circumference, with a second, tapered (i.e. frusto-conical) brake surface 112 defined on the inner circumference of the annular recess.

The inner circumference of the annular recess (i.e. the tapered brake surface 112) is tapered at a very small angle with the result that the recess is not strictly "annular" in shape, but for the purposes of this description, the term "annular" is to be interpreted to include an annulus with a slightly tapered inner wall.

A number of lock elements in the form of balls 114 are held captive inside the annular recess 110 by the wall of the sleeve 102, i.e. between the cylindrical and tapered brake surfaces 104,112. The brake element 94,100 is shaped and dimensioned such that the balls 14 fit inside the recess 110 with a slight clearance at the wider, lower end of the recess, such that the balls fit inside the recess with an interference fit higher in the recess.

The impact brake element 94,100 is shown in FIG. 4A in a fully extended condition, with the protuberance 108 extending far outside the top of the sleeve 102. A compression coil spring (not shown) is provided inside the sleeve 102, below the probe 106, to urge the probe upwardly towards its fully extended position. The lower end of the sleeve 102 is attached to the bottom flange 22 or one of the bars 68, as the case may be, and the top end of the protuberance 108 can be attached to the relevant displaceable part 92,98 or can simply be positioned so that the underside of the displaceable part can press longitudinally against the end of the protuberance.

Each of the impact brake elements 94,100 is normally in this extended condition and is held in this condition by its coil spring, but as the relevant displaceable part 92,98 is displaced relative to the remainder of the brace 10, it presses the probe 106 towards the sleeve 102, to slide further inside the sleeve against the bias of the spring.

Referring to FIG. 4B, if the probe 106 is caused to slide longitudinally downwardly into the sleeve at a relative low rate, the balls 114 are held at the lower end of the recess 110 by gravity and there is thus a clearance between the balls and the respective braking surfaces 104,112, so that the sliding movement can continue without interference.

However, referring to FIG. 4C, if the probe 106 is caused to slide longitudinally downwardly into the sleeve 102 at a relative high rate, e.g. under an impact load, the inertia of the balls 114 cause them not to follow the rapid downward movement of the probe at the same rate, with the result that the balls slide upwardly relative to the recess 110 (because the probe and balls are sliding downwardly at different rates). At the higher position of the balls 114 in the recess 110, the circumference of the tapered brake surface 112 is wider and the balls are urged outwardly by the tapered brake surface to become locked between the tapered and cylindrical brake surfaces 112,104 in a taper lock.

The dimensions and particularly the tolerances and clearances of the balls 114 and brake surfaces 104,112 can be dimensioned to allow downward movement of the probe 106 relative to the sleeve 102 without interference if the rate of relative movement between the probe and the sleeve is below a predetermined rate and to activate the taper lock as described herein above, when the rate of relative movement of the probe into the sleeve exceeds the predetermined rate.

It is to be understood that in the illustrated example of the present invention, the balls 114 are biased downwardly towards the wider end of the annular recess 110 by gravity. It is possible to enhance this bias or to replace it by using another biasing element such as a flexible element in the annular recess 110 that presses against the balls 114. However, the simplicity of the illustrated configuration is shown for ease of understanding. Any other method of biasing balls 114 in the freely moving position is in keeping with the spirit of the invention.

Referring to all the drawings, in use, when a wearer needs to tilt his head far backwards, e.g. when a motorcyclist is tucking into an aerodynamic position on the motorcycle and needs to get his torso as low as possible on the motorcycle, the head can be tilted backwards at a moderate (safe) rate so that the bottom edge of the motorcyclist's helmet presses the rear displaceable part 92 to pivot downwardly at a rate lower than a predetermined rate, while pressing the probes of the rear impact brake elements 94 into their respective sleeves without interference, as described above with reference to FIG. 4B. If the rider tilts his head forward again, the impact brake elements 94 are extended by their coil springs and the rear displaceable part 92 pivots upwards.

However, in the event that the rider's head is tilted backwards rapidly, e.g. during a rear impact collision, whether the impact brake elements 94 are fully extended or only partly extended, the downward impact of the bottom of the helmet on the rear displaceable part 92 will cause the rapid downward movement of the displaceable part and of the probes 106, at a rate that is higher than the predetermined rate, and the downward movement of the probes relative to the sleeves 102 will be stopped by the taper lock as described above, with reference to FIG. 4C. The result is that the impact load from the helmet is transferred from the displaceable part 92 along a load path via the locked rear impact brake elements 94 to the bars 68 and thus to the rider's body, to inhibit excessive head movement and to reduce the risk of injury to the rider's neck and upper spine.

The same applies to the front displaceable part 98 that can be pivoted downwardly and slid rearwards at rates lower than a predetermined rate by a pressing the bottom edge of the helmet against the front displaceable part. In the event of an impact, e.g. a front impact collision that tends to cause the rider's head to rotate forward, the front displaceable part 98 will be pressed towards the wearer's chest at a rate exceeding the predetermined rate and the front impact brake elements 100 will be locked by their taper lock and will transfer the impact load along a load path from the helmet and displaceable part 98 to the chest bearing surface 44 and to the chest of the rider, to inhibit excessive head movement and to reduce the risk of injury to the rider's neck and upper spine.

In addition to the advantages of the neck brace 10 mentioned above, the provision of two bars 68 spaced from the centre of the wearer's back, allows the brace to be worn comfortably with clothing such as motorcycling apparel that includes an aerodynamic protuberance or "hump" on the wearer's back, for preventing a vacuum behind the wearer's helmet at high speed. Further, the front bottom flange 22 defines a recess 116 which allows the wearer easy access to zippers or the like, that is often positioned centrally on the front of garments such as motorcycling apparel and/or to prevent discomfort by pressing on such zippers or the like.

What is claimed is:

1. A neck brace comprising:
    at least one impact surface which, when said brace is used with a helmet, limits movement of said helmet by contacting an underside of said helmet, wherein at least part of said impact surface is displaceable towards the body of a wearer of said neck brace;
    at least one bearing surface which is shaped and configured for bearing on the body of a wearer of said brace;
    a structure extending between said impact surface and said bearing surface having sufficient resilience to transfer impact loads of said helmet on said impact surface, to said wearer's body; and
    a brake element, extending between said impact surface and at least one of said structure and said bearing surface, said brake element configured to permit said displacement of said impact surface at rates slower than a predetermined rate of displacement and to resist said displacement if the rate of displacement exceeds said predetermined rate.

2. A neck brace of claim 1, further comprising:
    a pivotal joint connecting said displaceable part to the remainder of said neck brace.

3. A neck brace of claim 2, wherein said pivotal joint is configured to permit pivotal, as well as sliding displacement of said displaceable part relative to the remainder of said neck brace.

4. A neck brace of claim 1, wherein said displaceable part comprises:
    a rear displaceable part at the rear of said neck brace which is downwardly pivotable towards the upper back of a wearer of said neck brace.

5. A neck brace of claim 1, wherein said displaceable part comprises:
    a front displaceable part at the front of said neck brace which is downwardly pivotable towards the chest of said wearer.

6. A neck brace of claim 5, wherein said front displaceable part is configured to slide rearwards towards said wearer's chest during said pivotal movement.

7. A neck brace of claim 1, wherein said brake element comprises:
    a first component defining a first brake surface;
    a second component defining a second brake surface, wherein said second brake surface is displaceable relative to said first component when said displaceable part is displaced relative to said neck brace, and wherein said first and second braking surfaces extend at an acute angle relative to each other; and
    at least one lock element disposed between said first and second brake surfaces, wherein said lock element is configured to allow movement between said first and second components at rates lower than a predetermined rate and to engage said first and second brake surfaces in a taper lock, when displacement between said two components occurs at a rate exceeding said predetermined rate.

8. A neck brace of claim 7, wherein said first brake surface is a cylindrical surface and said second brake surface is a frusto-conical surface.

9. A neck brace of claim 8, wherein said first component is an outer cylindrical sleeve and said second component is elongate in shape and is longitudinally displaceable with at least part of said second component inside said sleeve, said second component including a protuberance that protrudes outside said sleeve.

10. A neck brace of claim 9, wherein an annular recess is defined around said second component and wherein said second brake surface is defined on the inner circumference of said annular recess and wherein said at least one lock element is held captive inside said annular recess.

11. A neck brace useable with a helmet comprising:
    at least one bearing surface configured to be worn on the body of a wearer of said brace;
    at least one impact surface configured to limit movement of said helmet through contact with an underside of said helmet, wherein at least part of said impact surface is displaceable towards said bearing surface; and
    a structure extending between said impact surface and said bearing surface configured to transfer impact loads of said helmet on said impact surface to said bearing surface; and
    a brake element extending between said impact surface and at least one of said structure and said bearing surface, said brake element configured to permit said displacement of said impact surface at rates slower than a predetermined rate of displacement, and to resist said displacement of said impact surface if the rate of displacement exceeds said predetermined rate.

12. The neck brace of claim 11, further comprising:
a pivotal joint connecting said displaceable part of said impact surface and the remainder of said neck brace.

13. The neck brace of claim 12, wherein said pivotal joint is configured to permit pivotal and sliding displacement of said displaceable part of said impact surface relative to the remainder of said neck brace.

14. The neck brace of claim 11, wherein said displaceable part of said impact surface comprises:
a rear displaceable part at the rear of said neck brace configured to downwardly pivot towards the upper back of a wearer of said neck brace.

15. The neck brace of claim 11, wherein said displaceable part of said impact surface comprises:
a front displaceable part at the front of said neck brace configured to downwardly pivot towards the chest of said wearer.

16. The neck brace of claim 15, wherein said front displaceable part is configured to slide rearwards towards said wearer's chest during said pivotal movement.

17. The neck brace of claim 11, wherein said impact brake element comprises:
a first component which defines a first brake surface;
a second component defining a second brake surface, wherein said second brake surface is displaceable relative to said first component when said displaceable part is displaced relative to said neck brace, and wherein said first and second braking surfaces extend at an acute angle relative to each other; and
at least one lock element disposed between said first and second brake surfaces, wherein said lock element is configured to allow movement between said first and second components at rates lower than a predetermined rate and to engage said first and second brake surfaces in a taper lock, when displacement between said two components occurs at a rate exceeding said predetermined rate.

18. The neck brace of claim 17, wherein said first brake surface is a cylindrical surface and said second brake surface is a frusto-conical surface.

19. The neck brace of claim 18, wherein said first component is an outer cylindrical sleeve and said second component is elongate in shape and is longitudinally displaceable with at least part of said second component inside said sleeve, said second component including a protuberance that protrudes outside said sleeve.

20. The neck brace of claim 19, wherein an annular recess is defined around said second component and wherein said second brake surface is defined on the inner circumference of said annular recess and wherein said at least one lock element is held captive inside said annular recess.

* * * * *